United States Patent
Bos et al.

(10) Patent No.: US 11,401,220 B2
(45) Date of Patent: Aug. 2, 2022

(54) ALKANE OXIDATIVE DEHYDROGENATION (ODH)

(71) Applicant: SHELL OIL COMPANY, Houston, TX (US)

(72) Inventors: Alouisius Nicolaas Renée Bos, Amsterdam (NL); Guus Van Rossum, Amsterdam (NL); Ronald Jan Schoonebeek, Amsterdam (NL); Michael Johannes Franciscus Maria Verhaak, Amsterdam (NL)

(73) Assignee: SHELL USA, INC., Houston, TX (US)

( * ) Notice: Subject to any disclaimer, the term of this patent is extended or adjusted under 35 U.S.C. 154(b) by 0 days.

(21) Appl. No.: 16/079,291

(22) PCT Filed: Feb. 23, 2017

(86) PCT No.: PCT/EP2017/054160
§ 371 (c)(1),
(2) Date: Aug. 23, 2018

(87) PCT Pub. No.: WO2017/144584
PCT Pub. Date: Aug. 31, 2017

(65) Prior Publication Data
US 2019/0055177 A1  Feb. 21, 2019

(30) Foreign Application Priority Data
Feb. 26, 2016 (EP) .................................. 16157537

(51) Int. Cl.
*C07C 5/48* (2006.01)
*B01J 8/06* (2006.01)
(Continued)

(52) U.S. Cl.
CPC .................. *C07C 5/48* (2013.01); *B01J 8/04* (2013.01); *B01J 8/067* (2013.01); *B01J 23/002* (2013.01);
(Continued)

(58) Field of Classification Search
CPC ....................................................... C07C 5/48
See application file for complete search history.

(56) References Cited

U.S. PATENT DOCUMENTS

| 3,801,634 A | 4/1974 | Krabetz et al. |
| 4,681,674 A | 7/1987 | Graven et al. |
| (Continued) | | |

FOREIGN PATENT DOCUMENTS

| CN | 1795987 A | 7/2006 |
| EP | 0261264 A1 | 3/1988 |
| (Continued) | | |

OTHER PUBLICATIONS

International Search Report and Written Opinion received for PCT Patent Application No. PCT/EP2017/054160, dated Apr. 21, 2017, 12 pages.

(Continued)

*Primary Examiner* — Philip Y Louie
*Assistant Examiner* — Alyssa L Cepluch
(74) *Attorney, Agent, or Firm* — Shell USA, Inc.

(57) ABSTRACT

Processes and associated reaction systems for the oxidative dehydrogenation of an alkane containing 2 to 6 carbon atoms, preferably ethane or propane, more preferably ethane, are provided. In particular, a process is provided that comprises supplying a feed gas comprising the alkane and oxygen to a reactor vessel that comprises an upstream and downstream catalyst bed; contacting the feed gas with an oxidative dehydrogenation catalyst in the upstream catalyst bed, followed by contact with an oxidative dehydrogenation/oxygen removal catalyst in the downstream catalyst bed, to yield a reactor effluent comprising the alkene; and supplying an upstream coolant to an upstream shell space of the reactor vessel from an upstream coolant circuit and a downstream coolant to a downstream shell space of the reactor vessel from a downstream coolant circuit.

11 Claims, 1 Drawing Sheet

(51) Int. Cl.
  *B01J 8/04* (2006.01)
  *B01J 23/68* (2006.01)
  *B01J 27/057* (2006.01)
  *B01J 23/00* (2006.01)
  *B01J 23/652* (2006.01)
  *B01J 35/00* (2006.01)
  *B01J 23/28* (2006.01)
  *B01J 23/887* (2006.01)
  *C07C 11/04* (2006.01)

(52) U.S. Cl.
  CPC ............ *B01J 23/28* (2013.01); *B01J 23/6525* (2013.01); *B01J 23/686* (2013.01); *B01J 23/8877* (2013.01); *B01J 27/0576* (2013.01); *B01J 35/0006* (2013.01); *B01J 2208/0053* (2013.01); *B01J 2208/00221* (2013.01); *B01J 2208/00513* (2013.01); *B01J 2208/025* (2013.01); *C07C 11/04* (2013.01); *C07C 2523/18* (2013.01); *C07C 2523/20* (2013.01); *C07C 2523/22* (2013.01); *C07C 2523/28* (2013.01); *C07C 2523/42* (2013.01); *C07C 2523/44* (2013.01); *C07C 2523/50* (2013.01); *C07C 2523/644* (2013.01); *C07C 2523/648* (2013.01); *C07C 2523/652* (2013.01); *C07C 2523/68* (2013.01); *C07C 2523/72* (2013.01); *C07C 2523/745* (2013.01); *C07C 2523/847* (2013.01); *C07C 2523/887* (2013.01); *C07C 2527/057* (2013.01); *Y02P 20/52* (2015.11)

(56) References Cited

U.S. PATENT DOCUMENTS

| | | | |
|---|---|---|---|
| 4,899,003 A † | 2/1990 | Manyik | |
| 6,518,476 B1 | 2/2003 | Culp et al. | |
| 7,091,377 B2 | 8/2006 | Borgmeier et al. | |
| 2004/0147393 A1 | 7/2004 | Hibst et al. | |
| 2008/0177117 A1 | 7/2008 | Benderly et al. | |
| 2010/0256432 A1 | 10/2010 | Arnold et al. | |
| 2011/0008218 A1 † | 1/2011 | Woo | |
| 2011/0009666 A1 | 1/2011 | Rosen | |
| 2012/0315198 A1 † | 12/2012 | Evans | |
| 2013/0072717 A1 | 3/2013 | Olbert et al. | |
| 2015/0141727 A1 † | 5/2015 | Simanzhenkov | |

FOREIGN PATENT DOCUMENTS

| | | | |
|---|---|---|---|
| EP | 1894885 † | 3/2008 | |
| EP | 1894885 A1 | 3/2008 | |
| EP | 3026037 A1 | 6/2016 | |
| FR | 1471983 A | 3/1967 | |
| RU | 2209202 C2 | 7/2003 | |
| WO | WO-0185333 A2 * | 11/2001 | ............ B01J 19/244 |
| WO | 03064035 A1 | 8/2003 | |
| WO | 2010096909 A1 | 9/2010 | |
| WO | 2013148006 † | 10/2013 | |

OTHER PUBLICATIONS

International Search Report and Written Opinion Received for PCT Application No. PCT/EP2014/076546, dated Feb. 12, 2015, 10 pages.
Solsona et al., "Selective Oxidation of Propane and Ethane on Diluted Mo—V—Nb—Te Mixed-oxide Catalysts", Journal of Catalysis, vol. 252, Issue No. 2, Dec. 31, 2007, pp. 271-280.
Botella et al., "Selective Oxidative Dehydrogenation of Ethane on Movtenbo Mixed Metal Oxide Catalysts", Journal of Catalysis, vol. 225, Issue No. 2, Jul. 2004, pp. 428-438.
Hariott et al., "Chemical Reactor Design", 2003, pp. 127, 128 and 210.
Clyde, "Application of Mercury Penetration to Materials Analysis", Powder Technology, vol. 3, Issue No. 1, Oct. 1969-Jul. 1970, pp. 117-123.

* cited by examiner
† cited by third party

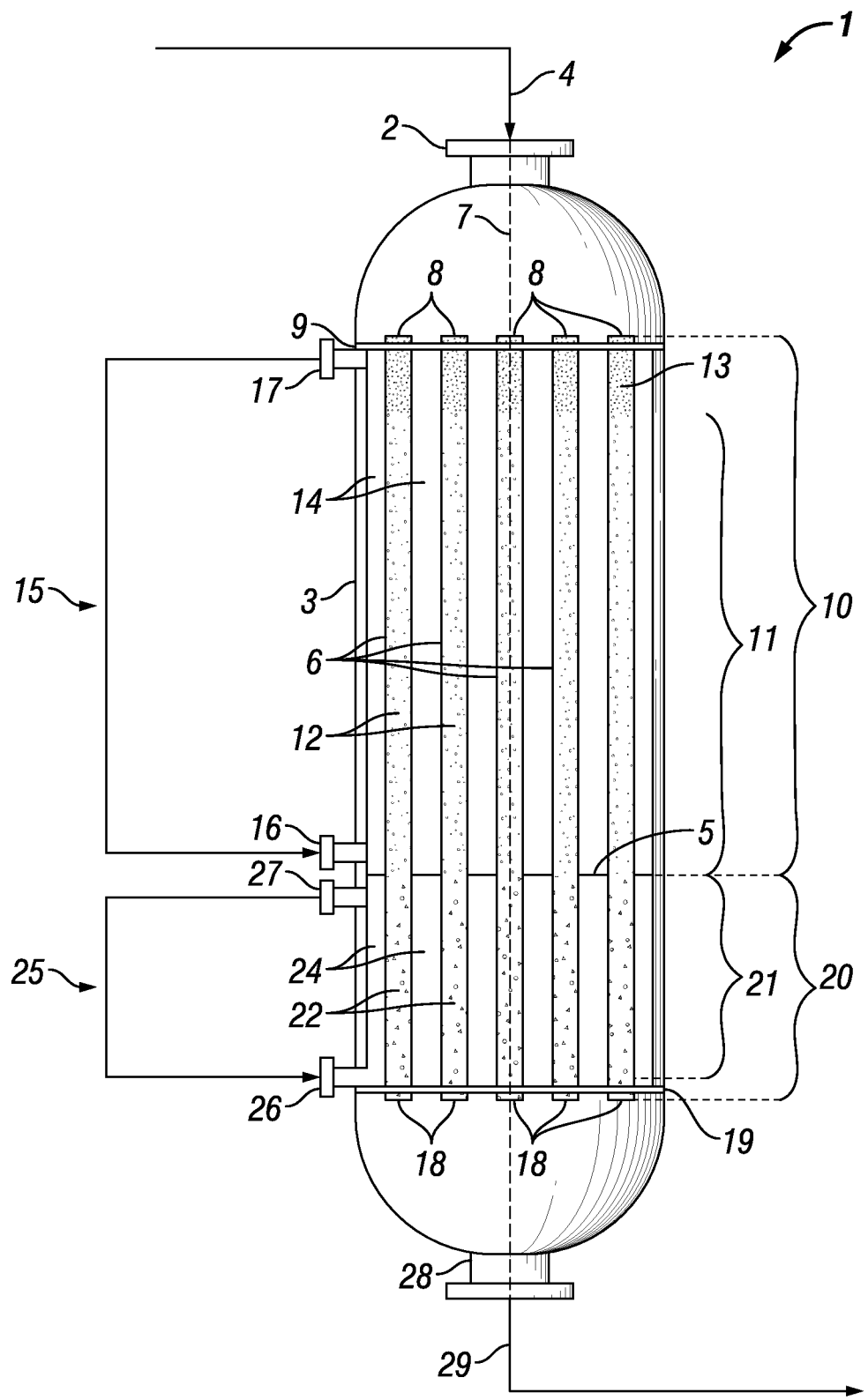

ALKANE OXIDATIVE DEHYDROGENATION (ODH)

CROSS REFERENCE TO RELATED APPLICATIONS

This is a national stage application of International Application No. PCT/EP2017/054160, filed 23 Feb. 2017, which claims benefit of priority to European Application No. 16157537.8, filed 26 Feb. 2016.

FIELD OF THE INVENTION

The present invention relates to processes and associated reaction systems for the oxidative dehydrogenation of an alkane containing 2 to 6 carbon atoms, in particular ethane or propane, more in particular ethane.

BACKGROUND

Ethylene is a valuable industrial compound that is widely employed as a raw material in the manufacture of polymers, styrene, ethylene oxide, vinyl chloride and vinyl acetate monomers, functionalized hydrocarbons (e.g., ethylbenzene, dichloroethane, acetaldehyde, ethanol, etc.), and many other chemical products that are used to produce a multitude of items, such as plastics, antifreeze, solvents, etc.

Currently, steam cracking of hydrocarbons (e.g., naptha, ethane, propane) is the most widespread process for the industrial manufacture of ethylene. In this process, steam-diluted alkanes are heated in a cracking furnace to a temperature sufficient to thermally crack the hydrocarbons (700-1000° C.) into alkenes, such as ethylene and propylene, in addition to a range of other hydrocarbons, hydrogen and coke. The residence time is very short, typically 0.1-0.5 seconds, and as a result of the high reactivity of the products, the product stream must be quenched immediately to maximize the production of the desired alkene and minimize the production of undesired by-products.

Although steam cracking is currently the industry standard for ethylene production, it has a variety of disadvantages. For example, steam cracking is highly endothermic and a highly energy-intensive process, thus necessitating a high fuel requirement. Similarly, because the process operates at very high temperatures, the requirements of the equipment are demanding. In addition, a significant amount of coke is formed inside the reactor, thus requiring frequent reactor shut-down for maintenance and coke removal.

An alternative method of ethylene preparation is via the oxidative dehydrogenation (ODH) of ethane. In this process, ethane is reacted with oxygen in the presence of an oxidative dehydrogenation catalyst to produce a product stream comprising predominately ethylene, along with unreacted reactants (such as ethane and oxygen), and typically other gases and/or by-products (such as carbon monoxide, carbon dioxide, water). Typically, the oxidative dehydrogenation catalyst is a mixed metal oxide catalyst containing molybdenum (Mo), vanadium (V), niobium (Nb) and preferably tellurium (Te) as the metals. Examples of alkane ODH processes, including catalysts and other process conditions, are for example disclosed in U.S. Pat. No. 7,091,377, U.S. Patent Publication Nos. 2004/0147393 and 2010/0256432, and WIPO Publication Nos. WO2003/064035 and WO2010/096909. Advantageously, alkane ODH processes are thermodynamically favored and can be carried out at potentially lower reaction temperatures, as compared to conventional steam-cracking, without coke formation.

Given the potential benefits over conventional alkene production processes, alkane ODH processes have been the subject of considerable research. In particular, processes to improve catalyst performance during continuous operation so as to extend catalyst life and/or maintain or improve catalyst activity and/or selectivity are currently being investigated. For example, EP 14194883 describes an improved ODH process utilizing a catalyst bed of mixed metal oxide catalyst comprising molybdenum, vanadium, niobium and preferably tellurium, wherein catalyst performance (e.g., selectivity, activity and/or stability) is improved by ensuring that a sufficiently high oxygen partial pressure is maintained throughout the catalyst bed (e.g., by controlling the oxygen concentration in the ODH reactor outlet gas).

However, in an industrial-scale ODH process, it would generally be considered undesirable to have a high oxygen concentration in the ODH reactor outlet gas due, at least in part, to the increased cost that would be associated with the subsequent removal of that oxygen in downstream processing. That is to say, for the above-mentioned catalyst performance improvements to be realized, a separate and costly "oxygen removal" step would typically be required (e.g., utilizing an oxygen elimination reactor positioned downstream from the ODH reactor) in order to avoid flammability/safety concerns in downstream processing.

Accordingly, the present inventors have sought to provide improved processes and reaction systems for the oxidative dehydrogenation of an alkane containing 2 to 6 carbon atoms, in particular ethane or propane, more in particular ethane. In particular, the present inventors have sought to provide ODH processes and reaction systems wherein catalyst performance (e.g., stability, activity and/or selectivity) is improved, whilst still yielding a low oxygen concentration in the ODH reactor outlet gas.

SUMMARY

In one aspect, a process for the oxidative dehydrogenation of an alkane containing 2 to 6 carbon atoms, preferably ethane or propane, more preferably ethane, to an alkene containing 2 to 6 carbon atoms, preferably ethylene or propylene, more preferably ethylene, is provided, the process comprising:

supplying a feed gas comprising the alkane and oxygen to an inlet of a reactor vessel, the reactor vessel comprising a reactor shell, a plurality of reactor tubes disposed within an interior of the reactor shell, and a perforated partition that divides the interior of the reactor vessel into an upstream region and a downstream region, wherein the plurality of reactor tubes comprise:

(i) an upstream catalyst bed positioned within the upstream region that comprises an oxidative dehydrogenation catalyst comprising tellurium, and (ii) a downstream catalyst bed positioned with the downstream region that comprises an oxidative dehydrogenation/oxygen removal catalyst;

contacting the feed gas with the oxidative dehydrogenation catalyst in the upstream catalyst bed, followed by contact with the oxidative dehydrogenation/oxygen removal catalyst in the downstream catalyst bed, to yield a reactor effluent comprising the alkene; and supplying an upstream coolant to an upstream shell space of the reactor vessel from an upstream coolant circuit and a downstream coolant to a downstream shell space of the reactor vessel from a downstream coolant circuit.

Further, in accordance with another aspect, a reaction system for the oxidative dehydrogenation of an alkane containing 2 to 6 carbon atoms, preferably ethane or propane, more preferably ethane, to an alkene containing 2 to 6 carbon atoms, preferably ethylene or propylene, more preferably ethylene, is provided, the reaction system comprising:

a reactor vessel that comprises a feed gas inlet fluidly connected to a source of alkane and oxygen, a reactor shell, a perforated partition that divides the interior of the reactor vessel into an upstream region and a downstream region, and a plurality of reactor tubes disposed within an interior of the reactor shell comprising:
(i) an upstream catalyst bed positioned within the upstream region that comprises an oxidative dehydrogenation catalyst comprising tellurium, and
(ii) a downstream catalyst bed positioned with the downstream region that comprises an oxidative dehydrogenation/oxygen removal catalyst;

an upstream coolant circuit fluidly connected to an upstream shell space of the reactor vessel; and a downstream coolant circuit fluidly connected to a downstream shell space of the reactor vessel.

BRIEF DESCRIPTION OF THE DRAWINGS

Some specific example embodiments of the disclosure may be understood by referring, in part, to the following description and the accompanying drawing.

The FIGURE is a schematic illustration showing an exemplary embodiment of the present disclosure.

While the present disclosure is susceptible to various modifications and alternative forms, specific example embodiments have been shown in the FIGURE and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DETAILED DESCRIPTION

It has now been found that an oxidative dehydrogenation catalyst comprising tellurium is particularly susceptible to catalyst deactivation in a reducing environment (e.g., a non-oxidizing environment). Such catalyst deactivation is typically manifested as an undesirable loss in catalyst stability, activity and/or selectivity. Further, it has also been found that when an oxidative dehydrogenation catalyst comprising tellurium is operated at a low oxygen partial pressure and a relatively high temperature (e.g., greater than 340° C.), tellurium may be lost from the catalyst, which can lead to serious problems in downstream equipment and process streams.

It is possible to minimize such catalyst deactivation and tellurium loss by limiting the amount of oxygen that is converted in the reaction and thus ensuring that a sufficiently high oxygen partial pressure is maintained throughout the catalyst bed. However, this method of operation leads to an increased oxygen concentration in the reactor effluent, which typically needs to be reduced in a separate and costly "oxygen removal" step due to potential downstream flammability/safety concerns.

The present inventors have surprisingly found that, by utilizing the processes and reaction systems disclosed herein, it is possible to minimize or avoid the above-mentioned problems, while simultaneously achieving a sufficiently low oxygen concentration in the reactor effluent without the need for a separate and costly "oxygen removal" step. In particular, it has surprisingly been found that these advantages may be achieved by supplying a feed gas comprising the alkane and oxygen to a reactor vessel that contains an upstream catalyst bed comprising an oxidative dehydrogenation catalyst comprising tellurium, and a downstream catalyst bed comprising an oxidative dehydrogenation/oxygen removal catalyst. In accordance with the present disclosure, the reactor vessel is divided by a perforated partition into an upstream region and a downstream region, with the upstream catalyst bed being positioned within the upstream region and the downstream catalyst bed being positioned within the downstream region. Coolant is independently circulated in the upstream and downstream shell spaces of the reactor vessel, thus providing for the independent control of the temperature within the upstream and downstream regions.

In general, the processes of the present disclosure are operated such that the upstream catalyst bed, which comprises an oxidative dehydrogenation catalyst comprising tellurium, is in an oxidizing environment and further downstream, where a majority of the oxygen has been consumed, is the downstream catalyst bed, which comprises an oxidative dehydrogenation/oxygen removal catalyst. Suitably, the oxidative dehydrogenation/oxygen removal catalyst in the downstream catalyst bed is a catalyst capable of catalyzing the reaction between alkane and oxygen to produce alkene at a low oxygen partial pressure without experiencing, or in any case much less, loss of activity. Thus, by operating in accordance with the processes of the present disclosure, a high concentration of oxygen in the reactor effluent is avoided, yet alkane is still reacted with the oxygen remaining in the downstream region so that it is converted into alkene without experiencing a significant decline in terms of catalyst performance due to the reduced oxygen concentration in the downstream region.

The reaction systems of the present disclosure generally comprise a reactor vessel, said reactor vessel comprising a feed gas inlet, a reactor shell, a perforated partition that divides the interior of the reactor vessel into an upstream region and a downstream region, and a plurality of reactor tubes comprising an upstream catalyst bed and a downstream catalyst bed. Suitably, the reaction system further comprises an upstream coolant circuit that is in fluid communication with an upstream shell space of the reactor vessel and an upstream coolant source, and a downstream coolant circuit that is in fluid communication with a downstream shell space of the reactor vessel and a downstream coolant source.

While the size and number of reactor tubes within a reactor vessel may vary widely from reactor to reactor, a reactor tube used in a commercial reactor vessel may generally have a length of from 1 to 25 meters and an internal tube diameter of from 10 to 80 millimeters. Further, the number of reactor tubes can vary and may range in the thousands, for example up to 50,000.

Within the reactor shell, the upper ends of the reactor tubes are typically fixed in place by an upper tube plate and are in fluid communication with the feed gas inlet of the reactor vessel. Similarly, the lower ends of the reactor tubes are typically fixed in place by a lower tube plate and are in fluid communication with an outlet of the reactor vessel. Preferably, the reactor tubes are arranged within the reactor shell in a substantially vertical manner such that they are no more than 5' from vertical, and the upper and lower tube plates are positioned within the reactor shell in a substantially horizontal manner such that they are no more than 3' from horizontal.

A perforated partition divides the reactor vessel into an upstream region and a downstream region. In general, the perforated partition is a plate having a plurality of holes through which the reactor tubes can pass. A perforated partition may be of any suitable material, such as metal (e.g., carbon steel).

Each reactor tube comprises an upstream catalyst bed positioned within the upstream region of the reactor vessel and a downstream catalyst bed positioned within the downstream region of the reactor vessel. Optionally, in addition to the upstream and downstream catalyst beds, the reactor tubes may further comprise one or more beds of an inert material, which may be positioned in the upstream region, the downstream region, or both.

Suitably, the upstream catalyst bed comprises an oxidative dehydrogenation catalyst comprising tellurium.

Examples of suitable oxidative dehydrogenation catalysts comprising tellurium include, but are not necessarily limited to, one or more mixed metal oxide catalysts having the following formula:

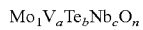

$$Mo_1V_aTe_bNb_cO_n$$

wherein:
a, b, c and n represent the ratio of the molar amount of the element in question to the molar amount of molybdenum (Mo);
a (for V) is from 0.01 to 1, preferably 0.05 to 0.60, more preferably 0.10 to 0.40, more preferably 0.20 to 0.35, most preferably 0.25 to 0.30;
b (for Te) is from >0 to 1, preferably 0.01 to 0.40, more preferably 0.05 to 0.30, more preferably 0.05 to 0.20, most preferably 0.09 to 0.15;
c (for Nb) is from >0 to 1, preferably 0.01 to 0.40, more preferably 0.05 to 0.30, more preferably 0.10 to 0.25, most preferably 0.14 to 0.20; and
n (for O) is a number which is determined by the valency and frequency of elements other than oxygen.

Optionally, the upstream catalyst bed may comprise more than one oxidative dehydrogenation catalyst comprising tellurium. For example, in one embodiment, the upstream catalyst bed may comprise a plurality of oxidative dehydrogenation catalysts having varied activity levels (e.g., so as to vary the activity level along the length of the reactor tube in the upstream region). Further, if desired, the upstream catalyst bed may further comprise inert material (e.g., to dilute and/or reduce the activity of the upstream catalyst bed).

Typically, the upstream catalyst bed has a catalyst bed height that is at least 50% of the reactor tube length, or at least 60%, or at least 65%, or at least 70%, on the same basis. In addition, the upstream catalyst bed typically has a catalyst bed height that is at most 99% of the reactor tube length, or at most 95%, or at most 90%, or at most 85%, on the same basis. Further, the upstream catalyst bed may have a catalyst bed height that is from about 50% to 99% of the reactor tube length, or from about 50% to 95%, or from about 70% to 95%, on the same basis.

Suitably, the downstream catalyst bed comprises an oxidative dehydrogenation/oxygen removal catalyst. In general, suitable oxidative dehydrogenation/oxygen removal catalyst are those catalyst capable of catalyzing the reaction between alkane and oxygen to produce alkene at a low oxygen partial pressure and/or catalyst used to drive oxygen to elimination.

Suitable oxidative dehydrogenation/oxygen removal catalysts include, but are not necessarily limited to, one or more mixed metal oxide catalysts having the following formula:

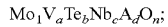

$$Mo_1V_aTe_bNb_cA_dO_n;\qquad a)$$

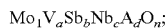

$$Mo_1V_aSb_bNb_cA_dO_n;\qquad b)$$

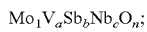

$$Mo_1V_aSb_bNb_cO_n;\qquad c)$$

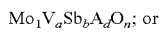

$$Mo_1V_aSb_bA_dO_n;\text{ or}\qquad d)$$

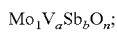

$$Mo_1V_aSb_bO_n;\qquad e)$$

wherein:
A is at least one metal selected from the group consisting of Pt, Pd, Cu, Ag and Fe;
a, b, c, d and n represent the ratio of the molar amount of the element in question to the molar amount of molybdenum (Mo);
a (for V) is from 0.01 to 1, preferably 0.05 to 0.60, more preferably 0.10 to 0.40, more preferably 0.20 to 0.35, most preferably 0.25 to 0.30;
b (for Te or Sb) is from >0 to 1, preferably 0.01 to 0.40, more preferably 0.05 to 0.30, more preferably 0.05 to 0.20, most preferably 0.09 to 0.15;
c (for Nb) is from >0 to 1, preferably 0.01 to 0.40, more preferably 0.05 to 0.30, more preferably 0.10 to 0.25, most preferably 0.14 to 0.20;
d (for A) is from >0 to 0.3; and
n (for O) is a number which is determined by the valency and frequency of elements other than oxygen.

Further, suitable oxidative dehydrogenation/oxygen removal catalysts may also include any known catalyst used to drive oxygen to elimination (e.g. oxidative catalysts, water-gas shift catalysts). For example, such catalysts may include supported platinum, palladium, silver, copper and/or iron catalysts, which are known to those skilled in the art.

Optionally, the downstream catalyst bed may comprise more than one oxidative dehydrogenation/oxygen removal catalyst. For example, in one embodiment, the downstream catalyst bed may comprise a plurality of oxidative dehydrogenation/oxygen removal catalysts having varied activity levels (e.g., so as to vary the activity level along the length of the reactor tube in the downstream region). Further, if desired, the downstream catalyst bed may further comprise inert material (e.g., to dilute and/or reduce the activity of the downstream catalyst bed).

Typically, the downstream catalyst bed has a catalyst bed height that is at least 1% of the reactor tube length, or at least 5%, or at least 10%, or at least 15%, on the same basis. In addition, the downstream catalyst typically has a catalyst bed height that is at most 50% of the reactor tube length, or at most 40%, or at most 35%, or at most 30%, on the same basis. Further, the downstream catalyst bed may have a catalyst bed height that is from about 1% to 50% of the reactor tube length, or from about 5% to 50%, or from about 5% to 30%, on the same basis.

Preferably, the oxidative dehydrogenation catalyst, the oxidative dehydrogenation/oxygen removal catalyst, or both is/are heterogeneous and in the form of particles. Further, preferably, said heterogeneous catalyst is porous, specifically a porous, particulate catalyst.

Optionally, a reaction system of the present disclosure may further comprise an oxygen removal zone, which comprises an oxygen removal catalyst, that is positioned downstream of both the upstream and downstream catalyst beds. When included, an oxygen removal zone may be positioned within the bottom portion of the reactor vessel (i.e. in the bottom portion of the reactor shell below the reactor tubes) and/or in a separate oxygen removal vessel. Advantageously, an oxygen removal zone may be used to further reduce the oxygen concentration of the reactor effluent. Suitable oxygen removal catalysts may include any known catalyst used to drive oxygen to elimination (e.g. oxidative catalysts, water-gas shift catalysts). For example, suitable oxygen removal catalysts may include supported platinum, palladium, silver, copper and/or iron catalysts, which are known to those skilled in the art.

A reaction system of the present disclosure further comprises an upstream coolant circuit and a downstream coolant circuit. As previously mentioned, regarding the structure of the reactor vessel, the reactor vessel is divided into an upstream region and a downstream region by a perforated partition, which correspondingly allows the temperatures of a coolant circulating in an upstream shell space and a downstream shell space to be independently controlled via the upstream and downstream coolant circuits, respectively. In general, the upstream and downstream coolant circuits supply coolant to and remove coolant from the upstream and downstream shell spaces of the reactor vessel, respectively.

Preferably, the upstream and downstream coolant circuits each comprise a cooling apparatus (e.g., heat exchanger, steam drum, etc.) and a circulation pump. Coolant may be supplied to, and removed from, the upstream and downstream shell spaces of a reactor vessel in any suitable manner. For example, coolant may be supplied to the upstream and downstream shell spaces of the reactor vessel at or near the bottom of the upstream and downstream regions, respectively, via upstream and downstream coolant inlets. Similarly, coolant may be removed from the upstream and downstream shell spaces of the reactor vessel at or near the top of the upstream and downstream regions, respectively, via upstream and downstream coolant outlets. The coolant may be any fluid suitable for heat transfer, for example, a molten salt or an organic material suitable for heat exchange (e.g., oil, kerosene, etc.).

Optionally, the heat that is removed from the reactor vessel using the upstream and/or downstream coolant circuit(s) may be used to heat the feed gas and/or the coolant that is supplied to the reactor vessel. Further, if desired, the removed heat may also be used for steam generation (or boiler feed water preheat) for use as an energy source, including as steam itself or further transformed into power.

In general, the respective temperatures of the coolant supplied to the upstream and downstream shell spaces of the reactor vessel are independently selected in such a manner that the relevant upstream or downstream catalyst bed has the desired activity. Further, as will be appreciated by one skilled in the art, the upstream and downstream coolant temperatures, as measured at the upstream and downstream coolant inlets, respectively, may be used to provide an approximation of the respective temperatures of the upstream and downstream catalyst beds. For example, depending upon the particular heat capacity of the coolant, process conditions and reactor specifications, the temperatures of the upstream and downstream catalyst bed may typically exceed that of the respective upstream and downstream coolant temperature by 1-30° C.

Suitably, the coolant temperature as measured at the upstream coolant inlet is typically at least 250° C., or at least 275° C., or at least 300° C., or at least 325° C., or at least 350° C., and typically at most 400° C., or at most 375° C., or most 370° C., or at most 360° C., or at most 350° C., or from 250° C. to 400° C., or from 275° C. to 375° C., or from 300° C. to 350° C.

Suitably, the coolant temperature as measured at the downstream coolant inlet is typically at least 120° C., at least 150° C., at least 200° C., at least 250° C., or at least 275° C., or at least 300° C., or at least 310° C., or at least 320° C., and typically at most 500° C., or at most 450° C., or at most 425° C., or at most 400° C., or at most 380° C., or from 120° C. to 500° C., or from 200° C. to 500° C., or from 250° C. to 500° C., or from 250° C. to 400° C., or from 300° C. to 400° C., or from 320° C. to 380° C.

In those embodiments where the downstream catalyst bed comprises a catalyst having an oxidative dehydrogenation functionality (i.e. catalyzes the reaction between alkane and oxygen to produce alkene), the temperature of the coolant as measured at the downstream coolant inlet is preferably from 300° C. to 500° C., or from 300° C. to 400° C.

Further, in those embodiments where the downstream catalyst bed comprises a catalyst having an oxidative functionality (i.e. catalyzes the combustion reaction of alkene and/or unreacted alkane to produce carbon dioxide and water) and/or a water-gas-shift functionality (i.e. catalyzes the reaction of carbon monoxide and water to produce carbon dioxide and hydrogen), the temperature of the coolant as measured at the downstream coolant inlet is preferably from 120° C. to 400° C., or from 150° C. to 400° C., or from 200° C. to 400° C.

Preferably, the pressure in the plurality of reactor tubes within the reactor vessel is from about 1 to 20 bara (i.e. "bar absolute"), preferably from 1 to 15 bara, more preferably from 2 to 10 bara, and even more preferably from 3 to 8 bara.

In accordance with the oxidative dehydrogenation processes of the present disclosure, a feed gas comprising an alkane and oxygen is supplied to the inlet of a reactor vessel. As used herein, the term "feed gas" is understood to refer to the totality of the gaseous stream at the inlet of the reactor vessel. Thus, as will be appreciated by one skilled in the art, the feed gas is often comprised of a combination of one or more gaseous stream(s), such as an ethane stream, an oxygen stream, a recycle gas stream, etc. Optionally, in addition to the alkane (e.g., ethane) and oxygen, the feed gas may further comprise other alkanes, carbon monoxide, carbon dioxide, hydrogen, steam, an inert gas (such as nitrogen, helium and/or argon), and/or various by-products of the ODH reaction (e.g., acetylene, acetic acid).

Suitable alkanes containing 2 to 6 carbon atoms generally include linear alkanes containing from two to six carbons atoms (i.e., ethane, propane, butane, pentane and hexane). Preferably, the alkane is a linear alkane containing from two to four carbon atoms (i.e., ethane, propane and butane). More preferably, the alkane is ethane or propane, most preferably ethane. In general, the alkane in the feed gas (e.g., ethane) may be from any suitable source, including natural gas, provided that impurities are sufficiently removed therefrom and may include fresh alkane and optionally, a recycle of unreacted alkane from the reactor effluent. Similarly, the oxygen may originate from any suitable source, such as air.

In general, the molar ratio of molecular oxygen to hydrocarbon (e.g., alkane, such as ethane) in the feed gas at the inlet of the reactor vessel may be in the range of from 0.01 to 1, more suitably 0.05 to 0.5. Preferably, the feed gas comprises from 5 to 35 vol. % of oxygen, relative to the total volume of the feed gas, more suitably 20 to 30 vol. % of oxygen, and 40 to 80 vol. % of alkane, more suitably 50 to 70 vol. % alkane, and less than 80 (0 to 80) vol. % of an inert gas, more suitably less than 50 (0 to 50) vol. % of an inert gas, more suitably 5 to 35 vol. % of an inert gas, most suitably 10 to 20 vol. % of an inert gas.

The order and manner in which the components of the feed gas are supplied to the inlet of the reactor vessel is not particularly limited, and therefore, the components may be combined simultaneously or sequentially. Further, the components of the feed gas may optionally be vaporized, preheated and mixed (if desired) prior to being supplied to the inlet of the reactor vessel using means known to those skilled in the art. For example, preheat techniques may include, for example, heat exchange from steam, a heat transfer fluid (e.g., coolant), reactor effluent, and/or a furnace.

The reactor effluent will typically comprise the dehydrogenated equivalent of the alkane (that is to say, the corresponding alkene). For example, in the case of ethane, the reactor effluent comprises ethylene, in the case of propane, the reactor effluent comprises propylene, and so on. In addition to an alkene, the reactor effluent may further comprise added water, if used, and additional water formed by the ODH reaction, carbon monoxide, carbon dioxide, carboxylic acids, and small amounts of other impurities, in addition to residual amounts of unreacted alkane and oxygen.

Preferably, the amount of oxygen in the reactor effluent is at most 500 parts per million by volume (ppmv), based on the total volume of the reactor effluent, or at most 300 ppmv, or at most 200 ppmv, or at most 100 ppmv, or at most 50 ppmv.

In some embodiments, an alkene may be further oxidized under the same conditions into the corresponding carboxylic acid, which may or may not contain one or more unsaturated double carbon-carbon bonds. For example, in the case of ethane, the reactor effluent may comprise ethylene and/or acetic acid. Further, in the case of propane, the reactor effluent may comprise propylene and/or acrylic acid.

Reference is now made to the FIGURE, which is a schematic view of a reaction system for the oxidative dehydrogenation of an alkane (e.g., ethane) to a corresponding alkene (e.g., ethylene), according to an embodiment of the present disclosure. It will be clear to the skilled person, that as a schematic diagram this FIGURE does not show all necessary inputs, outputs, recycle streams, etc. that may be present in the reaction system. Furthermore, in the FIGURE, as will be appreciated, elements can be added, exchanged, and/or eliminated so as to provide any number of additional embodiments. In addition, as will be appreciated, the proportion and the relative scale of the elements provided in the FIGURE are intended to illustrate the embodiments of the present disclosure, and should not be taken in a limiting sense.

As shown in the FIGURE, reactor vessel (1) is a shell-and-tube heat exchanger reactor vessel comprising feed gas inlet (2), reactor shell (3), perforated partition (5) that divides the interior of reactor vessel (1) into upstream region (10) and downstream region (20), and a plurality of open-ended reactor tubes (6) positioned substantially parallel to the central longitudinal axis (7) of reactor vessel (1). In general, perforated partition (5) is a plate having a plurality of apertures through which reactor tubes (6) can pass. The upper ends (8) of the reactor tubes (6) are connected to a substantially horizontal upper tube plate (9) and the lower ends (18) of the reactor tubes (6) are connected to a substantially horizontal lower tube plate (19). The upper tube plate (9) and the lower tube plate (19) are supported by the inner wall of reactor vessel (1).

As shown in the FIGURE, reactor tubes (6) pass through apertures present in perforated partition (5) such that a portion of each reactor tube is positioned within upstream region (10) and a portion of each reactor tube is positioned in downstream region (20). Reactor tubes (6) contain an upstream catalyst bed (11) positioned in upstream region (10) and a downstream catalyst bed (21) positioned in downstream region (20). In addition to an upstream and downstream catalyst bed, reactor tubes (6) may optionally further comprise a bed of inert material, such as inert bed (13). The upstream catalyst bed (11) contains an oxidative dehydrogenation catalyst comprising tellurium (12). The downstream catalyst bed (21) contains an oxidative dehydrogenation/oxygen removal catalyst (22). Typically, downstream catalyst bed (21) is supported in the reactor tubes (6) by a catalyst support means (not shown) arranged in the lower ends (18) of the reactor tubes (6).

Coolant is circulated through upstream shell space (14) and downstream shell space (24) in a substantially independent manner, thus providing for the independent control of the temperature within upstream region (10) and downstream region (20). Optionally, upstream shell space (14) and/or downstream shell space (24) may be provided with baffles (not shown) to guide coolant.

In upstream region (10), coolant is supplied from upstream coolant circuit (15) to upstream shell space (14) via one or more upstream coolant inlets, such as upstream coolant inlet (16), and is removed from upstream shell space (14) via one or more upstream coolant outlets, such as upstream coolant outlet (17). Similarly, in downstream region (20), coolant is supplied from downstream coolant circuit (25) to downstream shell space (24) via one or more downstream coolant inlets, such as downstream coolant inlet (26), and is removed from downstream shell space (24) via one or more downstream coolant outlets, such as downstream coolant outlet (27).

In both the upstream and downstream shell spaces, the circulating coolant will take up heat by contact with the reactor tubes (6) such that the coolant will typically be slightly hotter when withdrawn from the upstream or downstream coolant outlet than when it is supplied to the respective upstream or downstream coolant inlet. Suitably, in both the upstream and downstream coolant circuits, a cooling apparatus (not shown) may be used to remove heat from the coolant before it is re-supplied to the upstream and downstream shell spaces, respectively.

In accordance with the processes of the present disclosure, a feed gas (4) comprising ethane and oxygen is supplied to reactor vessel (1) via one or more feed gas inlets, such as feed gas inlet (3) which is in fluid communication with the upper ends (8) of the reactor tubes (6). In reactor tubes (6), feed gas (4) contacts upstream catalyst bed (11) first, followed by downstream catalyst bed (21). Contact of the feed gas in the presence of the catalyst at appropriate reaction conditions, as described above, converts at least a portion of the ethane to ethylene, water and reaction byproducts, if any. Reactor effluent (29) exits the reactor vessel (1) via one or more outlets, such as outlet (28) which is in fluid communication with the lower ends (18) of the reactor tubes (6).

That which is claimed is:

1. A process for the oxidative dehydrogenation of an alkane containing 2 to 6 carbon atoms to an alkene containing 2 to 6 carbon atoms comprising:
   supplying a feed gas comprising the alkane and oxygen to an inlet of a reactor vessel, the reactor vessel comprising a reactor shell, a plurality of reactor tubes disposed within an interior of the reactor shell, and a perforated partition that divides the interior of the reactor vessel into an upstream region and a downstream region, wherein the plurality of reactor tubes comprise:
   (i) an upstream catalyst bed positioned within the upstream region that comprises an oxidative dehydrogenation catalyst which is a mixed metal oxide catalyst comprising tellurium, and
   (ii) a downstream catalyst bed positioned within the downstream region that comprises an oxidative dehydrogenation catalyst which is a mixed metal oxide catalyst not comprising tellurium;

contacting the feed gas with the oxidative dehydrogenation catalyst in the upstream catalyst bed, followed by contact with the oxidative dehydrogenation catalyst in the downstream catalyst bed, wherein the process is operated such that the upstream catalyst bed is in an oxidizing environment, a majority of the oxygen is consumed in the upstream catalyst bed and the downstream catalyst bed has a reduced oxygen concentration compared to the upstream catalyst bed, to yield a reactor effluent comprising the alkene; and supplying an upstream coolant to an upstream shell space of the reactor vessel from an upstream coolant circuit and a downstream coolant to a downstream shell space of the reactor vessel from a downstream coolant circuit.

2. The process of claim 1, wherein the upstream catalyst bed has a catalyst bed height that is from 50 to 99% of the reactor tube length and the downstream catalyst bed has a catalyst bed height that is from 1% to 50% of the reactor tube length.

3. The process of claim 1, wherein the upstream coolant is supplied to the upstream shell space of the reactor vessel at a temperature of from 250° C. to 400° C.

4. The process of claim 1, wherein the reactor effluent comprises no more than 500 ppmv of oxygen.

5. The process of claim 1, wherein the oxidative dehydrogenation catalyst comprising tellurium in the upstream catalyst bed has the following formula:

$$Mo_1V_aTe_bNb_cO_n$$

wherein:
- a, b, c and n represent the ratio of the molar amount of the element in question to the molar amount of molybdenum;
- a is from 0.01 to 1;
- b is from >0 to 1;
- c is from >0 to 1; and
- n is a number which is determined by the valency and frequency of elements other than oxygen.

6. The process of claim 1, wherein the oxidative dehydrogenation catalyst in the downstream catalyst bed has one of the following formulas:

$$Mo_1V_aSb_bNb_cA_dO_n; \quad \text{a)}$$
$$Mo_1V_aSb_bNb_cO_n; \quad \text{b)}$$
$$Mo_1V_aSb_bA_dO_n; \text{ or} \quad \text{c)}$$
$$Mo_1V_aSb_bO_n; \quad \text{d)}$$

wherein:
- A is at least one metal selected from the group consisting of Pt, Pd, Cu, Ag and Fe;
- a, b, c, d and n represent the ratio of the molar amount of the element in question to the molar amount of molybdenum;
- a is from 0.01 to 1;
- b is from >0 to 1;
- c is from >0 to 1;
- d is from >0 to 0.3; and
- n (for O) is a number which is determined by the valency and frequency of elements other than oxygen.

7. The process of claim 1, wherein the alkane containing 2 to 6 carbon atoms is ethane or propane and the alkene containing 2 to 6 carbon atoms is ethylene or propylene.

8. The process of claim 1, wherein the alkane containing 2 to 6 carbon atoms is ethane and the alkene containing 2 to 6 carbon atoms is ethylene.

9. The process of claim 1, wherein the downstream coolant is supplied to the downstream shell space of the reactor vessel at a temperature of from 300° C. to 500° C.

10. The process of claim 1, wherein the amount of oxygen in the reactor effluent is at most 500 parts per million by volume (ppmv), based on the total volume of the reactor effluent, and wherein the feed gas at the inlet of the reactor vessel comprises from 5 to 35 vol. % of oxygen, relative to the total volume of the feed gas.

11. The process of claim 1, wherein the downstream catalyst bed has a catalyst bed height which is at most 30% of the reactor tube length.

* * * * *